United States Patent
Newman et al.

(10) Patent No.: US 7,824,569 B2
(45) Date of Patent: Nov. 2, 2010

(54) SOLUBLE SALT PRODUCED FROM A BIOPOLYMER AND A PROCESS FOR PRODUCING THE SALT

(75) Inventors: John K. Newman, Vicksburg, MS (US); David B. Ringelberg, Bradford, VT (US); Kevin P. O'Connell, Abingdon, MD (US); William A. Martin, Vicksburg, MS (US); Victor F. Medina, Vicksburg, MS (US); Steven L. Larson, Vicksburg, MS (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 247 days.

(21) Appl. No.: 12/243,084

(22) Filed: Oct. 1, 2008

(65) Prior Publication Data

US 2010/0078590 A1    Apr. 1, 2010

(51) Int. Cl.
C09K 3/22 (2006.01)
(52) U.S. Cl. ............... 252/88.1; 252/88.2; 405/265
(58) Field of Classification Search ............... None
See application file for complete search history.

(56) References Cited

U.S. PATENT DOCUMENTS

| | | |
|---|---|---|
| 4,592,931 A | 6/1986 | Cargle |
| 5,860,770 A | 1/1999 | Hunt |
| 5,934,839 A | 8/1999 | Mallon et al. |
| 6,689,204 B2 | 2/2004 | Stanley |
| 6,835,761 B2 | 12/2004 | Harrison |
| 7,288,581 B2 | 10/2007 | Ferrall et al. |

OTHER PUBLICATIONS

Chouly, C. et al., NMR Studies of Succinoglycan Repeating-Unit Octasaccharides from *Rhizobium meliloti* and *Agrobacterium radiobacter*, Int. J. Biol. Macromol. 17, 357-363, 1995.

Comte et al., Biosorption Properties of Extracellular Polymeric Substances (EPS) Towards Cd, Cu and Pb for Different pH Values, Jour. of Haz, Matls. 151, 185-193, 2008.

(Continued)

*Primary Examiner*—Necholus Ogden, Jr.
(74) *Attorney, Agent, or Firm*—Earl H. Baugher, Jr.

(57) ABSTRACT

Modifications to the extracellular polymeric substance, predominantly extracellular polysaccharide, of a biopolymer produced by *Rhizobium tropici* ATCC 49672 yield a stable dry salt transported more easily than a fluid or gel and more stable than either. The salt may be re-constituted with water on-site. Embodiments may be employed as a soil amendment for soil strengthening, reducing hydraulic conductivity, erosion control and dust control as well as a metal chelator for contaminant remediation. Based on comparison with dextran standards, an embodiment demonstrated a molecular weight over 511,000 D. Embodiments include a day salt that is precipitated from solution and in use is re-hydrated back to original form. When added to a sandy soil at 0.1% by dry weight, an embodiment decreased the hydraulic conductivity by three orders of magnitude. These properties make embodiments of the present invention an attractive, "green" alternative to petroleum-based synthetic polymers for such applications as rapid roadway construction and soil erosion prevention.

25 Claims, 3 Drawing Sheets

OTHER PUBLICATIONS

Newman, et al., Stabilization of Silty Sand Using Polymer Emulsions, IJP 4, 1-12, 2005.

Skorupska, A. et al., Rhizobial Exopolysaccharides Genetic Control and Symbiotic Functions, Microbial Cell Factories 5, 7, 19 pp, 2006.

Xu et al., Use of Slow Release Fertilizer and Biopolymers for Stimulating Hydrocarbon Biodegradation in Oil-Contaminated Beach Sediments, Mar. Poll. Bull 51, 1101-1110, 2005.

Yu et al., Extracellular Proteins, Polysaccharides and Enzymes Impact on Sludge Aerobic Digestion after Ultrasonic Pretreatment, Water Rsch. vol. 42 (8-9), 1924-1934, 2008.

SOLUBLE SALT PRODUCED FROM A BIOPOLYMER AND A PROCESS FOR PRODUCING THE SALT

STATEMENT OF GOVERNMENT INTEREST

Under paragraph 1(a) of Executive Order 10096, the conditions under which this invention was made entitle the Government of the United States, as represented by the Secretary of the Army, to an undivided interest therein on any patent granted thereon by the United States. This and related patents are available for licensing to qualified licensees. Please contact Bea Shahin at 217 373-7234.

BACKGROUND

Both synthetic and biopolymers are made of repetitive monomeric units. The term primary structure is used to describe the chemical composition and the sequence of the repeated units. Many synthetic polymers prepared using petroleum based monomers have a simple, non-varied structure and are typically random copolymers where the repeat unit sequence is statistically controlled. In contrast, many biopolymers can fold into functionally compact shapes through crosslinking (via hydrogen bonding, hydrophobic associations, multivalent ion coordination, and the like). This changes not only their shape, but their chemical properties. In addition, biopolymers often have complex pendant moieties that display highly specific functionalities. The mono-dispersity and specific structure available in biopolymers provide distinct advantages over the poly-dispersity and random structure encountered in many synthetic polymers.

*Rhizobium tropici* ATCC® 49672 is a catalogued symbiotic nodulator of leguminous plants. Martinez-Romero et al., *Rhizobium tropici*, a Novel Species Nodulating *Phaseolus vulgaris* L. Beans and *Leucaena* sp. Trees, Int. J. Syst. Bacteriol. 41, 417-426, 1991. *Rhizobium tropici* is also known for its production of a gel-like, extracellular polymeric substance (EPS). Gil-Serrano, A. et al., Structure of the Extracellular Polysaccharide Secreted by *Rhizobium leguminosarum* var. *phaseoli* CIAT 899, Carbohydr. Res. 204, 103-107, 1990. Most of the *Rhizobium*-produced EPS are polysaccharides containing glucuronic acid. Dudman, W. F. et al., The Structure of the Acidic Polysaccharide Secreted by *Rhizobium phaseoli* Strain 127 K36, Carbohydr. Res. 117, 141-156, 1983a; Dudman, W. F., et al., The Structure of the Acidic Polysaccharide Secreted by *Rhizobium phaseoli* Strain 127 K87, Carbohydr. Res. 117, 169-183, 1983b; Franzén, L. E. et al., The Structure of the Acidic Polysaccharide Secreted by *Rhizobium phaseoli* Strain 127 K44, Carbohydr. Res. 117, 157-167, 1983. Some exceptions to this structure have been reported. Amemura, A. and T. Harada, Structural Studies on Extracellular Acidic Polysaccharides Secreted by Three Non-Nodulating *Rhizobia*, Carbohydr. Res. 112, 85-93, 1983; Gil-Serrano et al. (1990). Studies of the structure of these polymers have been reviewed by Laspidou and Rittmann. Laspidou, C. S. and B. E. Rittmann, A Unified Theory for Extracellular Polymeric Substances, Soluble Microbial Products, and Active and Inert Biomass, Wat. Res. 36, 2711-2720, 2002. The functions of the EPS include surface adhesion, self-adhesion of cells into biofilms, formation of protective barriers, water retention around roots, and nutrient accumulation. Laspidou and Rittmann (2002).

Refer to FIG. 5. Protonation of the hydrolytic acid functional groups 502 allows the reaction between these groups and amine functional groups 501 within the polymer, or adjacent polymers. The carboxyl group 502A reacts with the biopolymer amino group 501 releasing water 504 in a dehydration synthesis. The derivative is a polydentate ligand 503 suitable for metals sequestration.

EPS from *Rhizobium tropici* has unique adhesive and protective biofilm formation qualities. Given that production and transportation issues are addressed, the adhesion and water retention characteristics of ex situ "grown" EPS may be useful for dust and erosion control in situations where traditional techniques are not viable. Commercially, there are numerous products available that are employed for both dust control and soil strengthening. Nontraditional soil strengthening amendments have been investigated for many years and include ionic, enzymatic, lignosulfonate, salt, polymer and tree resin stabilizers and petroleum resins. Tingle, J. S. et al., Constitutive Analyses of Nontraditional Stabilization Additives, ERDC TR-04-5, U.S. Army Corps of Engineers, Engineer Research and Development Center, Vicksburg, Mass., 2004. These non-traditional amendments act by coating the soil particles and forming strong physical bonds with the soil. Newman, K. et al., Stabilization of Silty Sand Using Polymer Emulsions, IJP 4, 1-12, 2005. Unlike EPS biopolymers, these static molecules do not have the capacity for secondary reactions, such as crosslinking or ion exchange, which may be a key factor in strengthening the bonds between the biopolymer and the soil and have been found to be less effective when compared to petrochemical soil stabilizers. Synthetic, petroleum-based soil additives, packaged as emulsions, are gaining popularity due to their ease of handling and lower safety and environmental concerns compared to traditional soil stabilization agents such as asphalt, Portland cement, and lime. The majority of soil-stabilizing emulsions are copolymers of ethylene or vinyl acetate or are acrylic copolymers. National Resource Conservation Service, Conservation Practice Standard Anionic Polyacrylamide (PAM) Erosion Control, Code 450. These petroleum-based additives produce amended soils with improved engineering properties. Soil-stabilizing polymers, when mixed with soils, may exhibit strengths similar to that of Portland cement but impart more flexibility to the soil, i.e. increase toughness. This translates into increased resistance to cracking due to a higher ultimate failure strain before yield. Newman et al. (2005).

EPS are being investigated for use in a wide range of commercial, medical, and industrial applications. Specific applications include adsorption of heavy metals from wastewater and natural water (Comte et al., Biosorption Properties of Extracellular Polymeric Substances (EPS) Towards Cd, Cu, and Pb for Different pH Values, Jour. of Haz, Matls. 151, 185-193, 2008; Noghabi et al., The Production of a Cold-Induced Extracellular Biopolymer by *Pseudomonas Fluroscens* BM07 under Various Growth Conditions and its Role in Heavy Metals Absorption, Process Biochem. 42, 847-855, 2007), bioremediation of polycylic aromatic hydrocarbons in oil-contaminated beach sand (Xu et al., Use of Slow Release Fertilizer and Biopolymers for Stimulating Hydrocarbon Biodegradation in Oil-Contaminated Beach Sediments, Marine Pollution Bull. 51, 1101-1110, 2005), and treatment of activated sludge (Sheng et al., Characterization of Adsorption Properties of Extracellular Polymeric Substances (EPS) Extracted from Sludge, Colloids and Surfaces B: Biointerfaces 62, 83-90, 2008), Yu et al., Extracellular Proteins, Polysaccharides and Enzymes Impact on Sludge Aerobic Digestion after Ultrasonic Pretreatment, Water Rsch. Vol. 42 (8-9), 1924-1934, 2008).

Current materials utilized for soil stabilization and dust control are synthetic petroleum-based materials. Many of these synthetic materials are non-biodegradable and persist long after their useful life as amendments. Thus, for one application, what is needed is an environmentally benign and biodegradable replacement for petroleum-based amendments that provides increased soil strength when mixed with soil for load-bearing applications such as walkways, paths, roads, airfields and the like. For yet another application what is needed is a similar benign and biodegradable amendment to limit dust formation by agglomerating soil particles together, preventing fine particle formation which may become airborne. For yet another application what is needed is a similar benign and biodegradable amendment that may be employed for contaminant remediation. Select embodiments of the present invention address these needs.

DETAILED DESCRIPTION

Figure 1:
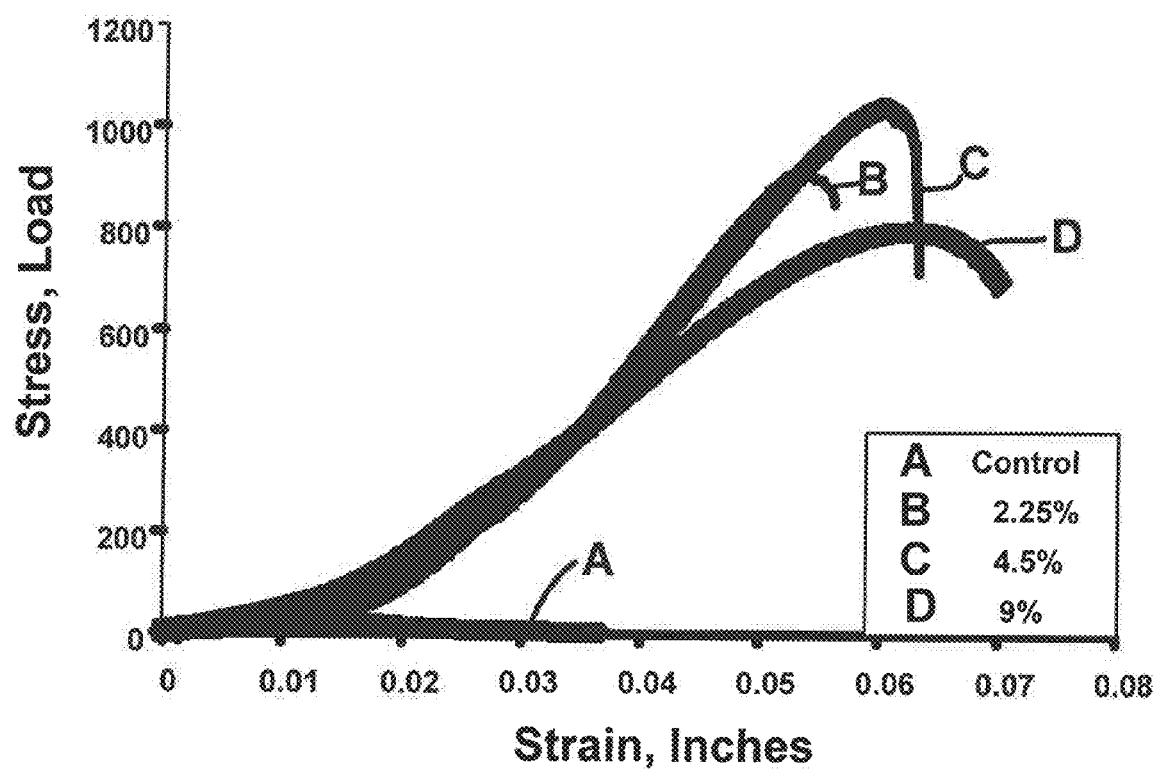
FIG. 1 is a graph depicting the increased strength of soil after *Rhizobium tropici* EPS is added ex situ under dry conditions as compared to a control.

In select embodiments of the present invention, a bacteria, *Rhizobium tropici*, produces a biopolymer ex situ that, when recovered from a bacterial culture and added to a soil, improves the engineering properties. Preliminary studies have demonstrated that significant strength gains, similar to those observed with synthetic polymers, can be realized by adding *Rhizobium tropici* EPS to silty sand soils. The use of biopolymers in engineering applications also reduces or eliminates the use or generation of hazardous substances in the design, manufacture, and use of the petroleum-based polymers currently in use as well as the use of petroleum in general. In general, biopolymers may also be modified to optimize the desired attributes for a particular use, thus they are application specific. For example, select embodiments of the present invention may be engineered to perform a specific task, such as metal chelation while simultaneously functioning as a soil binder to prevent transport of heavy metals with suspended solids. With the addition of specific functional groups to the EPS it becomes a heavy metal chelator as well as erosion/dust control agent. Modifications made to *Rhizobium tropici* EPS allow production of a transportable product that can be reconstituted with water at the location of use. This eliminates issues associated with competitive biological systems under in situ EPS production, and presents a logistic advantage over transport of liquid soil amendments such as the petroleum based polymeric amendments. In a specific application such as traditional small arms firing range (SAFR) maintenance, the addition of a non-polluting soil amendment with a smaller production carbon footprint may significantly reduce support costs for live fire (munitions) training.

Further, select embodiments of the present invention are inherently self-healing, thus providing a long term solution in such applications as berms for SAFR, Open Burning/Open Detonation (OB/OD) ranges, levees, road embankments, and the like. This results in reduced life cycle costs through reduced maintenance costs, decreased soil loss, and reduction in transport of environmental contaminants, in particular heavy metals, among other benefits. Finally, at the end of their useful life (if applicable) biopolymers may be treated (if necessary) to promote natural decomposition, consumed as food by soil bacteria.

Uses of select embodiments of the present invention include improving the strength of soil for load-bearing applications such as road bases, parking areas, construction platforms, helipads, and the like. Not only are strength gains to the unmodified soil realized, but the strain at which failure occurs is higher, indicating that the biopolymer provides increased flexibility (or toughness) to the soil. Improved engineering characteristics upgrade the load bearing and fracture resistance properties of native soils. For example, when added to soil at 0.1% by dry weight, the extracellular polysaccharide (EPS) produced by *Rhizobium tropici* ATCC® 49672 in select embodiments of the present invention decreases the hydraulic conductivity of the soil by three orders of magnitude.

In select embodiments of the present invention, modifications made to the EPS produced by *Rhizobium tropici* ATCC® 49672 produce a dry salt that precipitates from solution and can be re-hydrated back to its original form. This is particularly useful in situations where traditional techniques are not viable. This biopolymer may replace petroleum-based polymers currently used for the above applications. Unlike synthetic polymers based on monomeric components that either react immediately or wash away with added moisture, an EPS biopolymer salt adjusts to the buffering pH of a soil. One result is a soil amendment that remains in place and creates additional covalent linkages as the soil is disturbed, e.g., agitated, undergoes wet/dry cycles, and the like. Further; addition of small quantities of biopolymer may result in amide-forming condensation reactions that increase soil strength to levels equal to or beyond that achieved from the original application of the amendment.

In select embodiments of the present invention, a dry salt comprising a biopolymer of at least an extracellular polymeric substance (EPS) naturally produced by *Rhizobium tropici* is made by: placing a culture of *Rhizobium tropici* in a container of water/nutrients; maintaining the culture and water/nutrients for a pre-specified hold time to produce a first mixture of water/nutrients and EPS; decanting the first mixture to yield EPS and an aqueous fluid; precipitating the EPS with an alcohol to yield a first precipitate; adding to the first precipitate an hydroxide to dissolve the first precipitate by mixing the hydroxide with the first precipitate to yield a homogeneous second mixture with a pH above about 10; derivatizing the second mixture by adding a solid salt, mixing the salt with the second mixture to establish a homogeneous third mixture; isolating the third mixture in an alcohol to yield a second precipitate; decanting the alcohol, leaving the second precipitant; rinsing the second precipitant; and drying the rinsed second precipitant to yield the dry salt.

In select embodiments of the present invention, the container is one or more bioreactors.

In select embodiments of the present invention the *Rhizobium tropici* is *Rhizobium tropici* ATCC® 49672, the solid salt is NaCl and the alcohol is ethanol added in the volume ratio of 1:2 ethanol to the mixture.

In select embodiments of the present invention, the hydroxide is added in a quantity to yield a pH above about 10.

In select embodiments of the present invention the water is distilled deionized water and said first salt is added to provide a 0.1 normal sodium chloride solution.

In select embodiments of the present invention the EPS comprises one or more extracellular polysaccharides.

In select embodiments of the present invention the pre-specified hold time is about one hour.

In select embodiments of the present invention, a method of manufacturing a dry salt comprising a biopolymer of at least an extracellular polymeric substance (EPS) naturally produced by Rhizobium tropici, comprises: placing a culture of said Rhizobium tropici in one or more containers of water/nutrients; maintaining the culture and water/nutrients for a specified hold time to produce a first mixture comprising water/nutrients and EPS; decanting the first mixture to yield EPS; precipitating the EPS with an alcohol to yield a first precipitate; adding to the first precipitate one or more hydroxides to dissolve the first precipitate by mixing the hydroxide with the first precipitate to yield a homogeneous second mixture with a pH above about 10; derivatizing the second mixture by adding one or more solid salts, mixing the added solid salt with the second mixture to establish a homogeneous third mixture; isolating the third mixture in an alcohol to yield a second precipitate and an alcohol fluid; decanting the alcohol, leaving a second precipitant; rinsing the second precipitant one or more times; and drying the rinsed second precipitant to yield the dry salt.

In select embodiments of the present invention, the method employs a bioreactor as the container.

In select embodiments of the present invention the method employs Rhizobium tropici ATCC® 49672 as a culture, NaCl as a solid salt, and ethanol as an alcohol added in the volume ratio of approximately 1:2 ethanol to the mixture of the water/nutrients and the EPS.

In select embodiments of the present invention, the method adds sufficient hydroxide to yield a pH above about 10 for the second mixture.

In select embodiments of the present invention, the method employs distilled deionized water adding said first salt to provide a 0.1 normal sodium chloride solution.

In select embodiments of the present invention the method comprises re-cycling the aqueous fluid to the container for use in subsequent batch processing and distilling and re-cycling the alcohol fluid for re-use in precipitating the EPS in subsequent batch processing.

In select embodiments of the present invention the method yields an EPS comprising one or more extracellular polysaccharides.

In select embodiments of the present invention the method employs a pre-specified hold time of about one hour.

In select embodiments of the present invention, a soil amendment comprises: a dry salt comprising a biopolymer of an extracellular polymeric substance (EPS) naturally produced by Rhizobium tropici, the dry salt made by: placing a culture of Rhizobium tropici in one or more containers of water/nutrients; maintaining the culture and water/nutrients for a pre-specified hold time to produce a first mixture comprising water/nutrients and EPS; decanting the first mixture to yield EPS and an aqueous fluid; precipitating the EPS with an alcohol to yield a first precipitate; adding to each first precipitate one or more hydroxides to dissolve the first precipitate by mixing the hydroxide with the first precipitate to yield a homogeneous second mixture with a pH above about 10; derivatizing the second mixture by adding one or more solid salts, mixing the salt with the second mixture to establish a homogeneous third mixture; isolating the third mixture in an alcohol to yield, a second precipitate; decanting the alcohol, leaving the second precipitant; rinsing the second precipitant one or more times; and drying the rinsed second precipitant to yield the dry salt; and an aqueous solution to activate the dry salt.

In select embodiments of the present invention, a method for amending soil comprises: providing a dry salt comprising an extracellular polymeric substance (EPS) naturally produced by Rhizobium tropici, the dry salt made by: placing a culture of Rhizobium tropici in one or more containers of water/nutrients; maintaining the culture and water/nutrients for a pre-specified hold time to produce a first mixture comprising water/nutrients and EPS; decanting the first mixture to yield EPS and an aqueous fluid; precipitating the EPS with an alcohol to yield a first precipitate; adding to each first precipitate one or more hydroxides to dissolve the first precipitate by mixing the hydroxide with the first precipitate to yield a homogeneous second mixture with a pH above about 10; derivatizing the second mixture by adding one or more solid salts, mixing the added solid salt with the second mixture to establish a homogeneous third mixture; isolating the third mixture in an alcohol to yield a second precipitate; decanting the alcohol, leaving the second precipitant; rinsing the second precipitant one or more times; and drying the rinsed second precipitant to yield the dry salt; and mixing the dry salt with soil to amend the soil.

In select embodiments of the present invention, the method further comprises adding an aqueous solution to activate the dry salt. In select embodiments of the present invention, the method further comprises adding the aqueous solution to the dry salt prior to mixing the dry salt with the soil. In select embodiments of the present invention, the method further comprises mixing the dry salt with the soil at a weight ratio of about 1:1000 of dry salt to soil.

Figure 6:
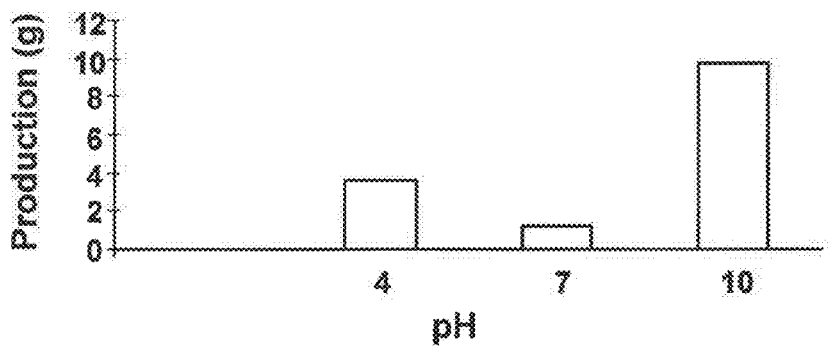
FIG. 6 depicts production of grams of biopolymer EPS of a select embodiment of the present invention versus pH for three values of pH.

In select embodiments of the present invention, biopolymer materials were dissolved in water solutions with elevated pH, filtered, and the resultant water/biopolymer solution used to produce salts of the biopolymer. See FIG. 6 for comparison of production levels in grams of a select embodiment of the present invention at three different pH levels, the highest pH of 10 having the greatest yield, a factor of about 6 over a neutral pH of 7. The elevated pH enabled an increase in the solubility of the biopolymer and solution by ionization of carboxylic acid and alcohol functionalities present as part of the biopolymer molecular structure. The resultant deprotonation of weakly acidic functionalities on the biopolymer that produces anionic sites of the biopolymer molecules increased the hydrophilicity of the polymer and served as ion pairing sites for precipitation as sodium biopolymer salts. Solid sodium chloride was added to produce a 0.1 normal sodium chloride solution. The solution was filtered to remove non-dissolved materials, and a volume of ethanol was added to the aqueous biopolymer solution and allowed to rest for one hour. The ethanol/water solution was then decanted, leaving the biopolymer cell mass. The resultant biopolymer salt was rinsed three times with ethanol and allowed to dry. The dried biopolymer salt was then evaluated with regards to its ability to dissolve into distilled water. The solid biopolymer salt dissolved in distilled water and produced a viscous solution.

Refer to FIG. 1 depicting performance of various concentrations of the hydrolyzed EPS compared to a control. All biopolymer from Rhizobium tropici for these tests was hydrolyzed in the supernatant, recovered by precipitation with ethanol, dried and added to the soil in controlled amounts. The soil was compacted at optimum moisture content (9%) and allowed to completely dry before testing. Data represent the average of three specimens for each curve.

Figure 2:
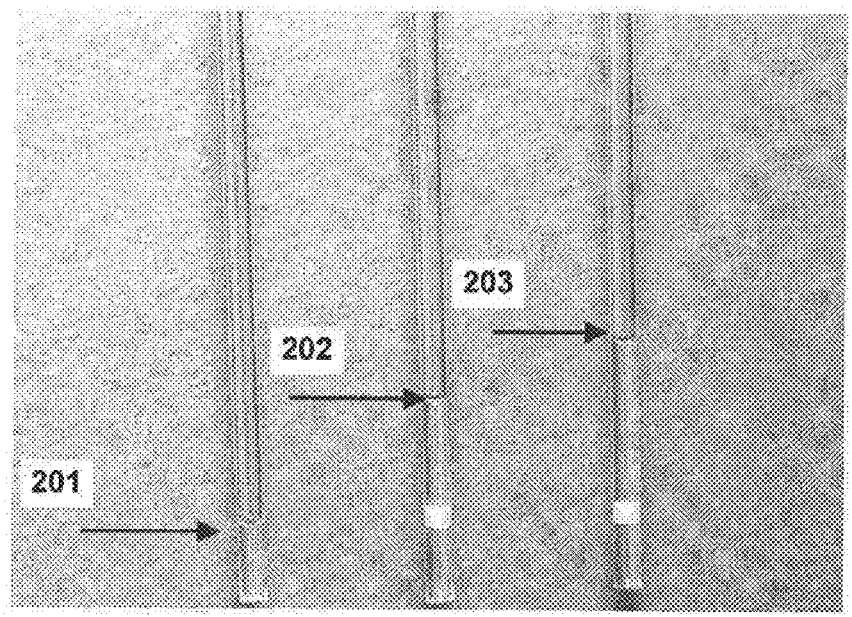
FIG. 2 is a photo depicting the relative surface tension of select embodiments of the present invention as compared to water and another biopolymer.

It is noteworthy that, from a practical standpoint, the *Rhizobium tropici* EPS displays interesting solution behavior. Refer to FIG. 2, a photograph showing two solutions of biopolymer, one from *Beyjerinkia indica* 202 and one from *Rhizobium tropici* 201, as compared to water 203. The level of the solution column 201, 202, 203 indicates the relative surface tension of each polymer. Note that the *Rhizobium tropici* solution 201 displays low surface tension compared to water 203. This is highly advantageous for conventional applications such as dust control, soil stabilization, and heavy metal leachate control where penetration of the active ingredient into the soil is needed.

In select embodiments of the present invention, *Rhizobium tropici* is interacted with a hydroxide ($OH^-$) to precipitate a biopolymer. NaCl is then added to prepare for a precipitation in ethanol. The resultant precipitant is then washed and dried to yield a water-soluble salt.

Modifications made to the EPS produced by *Rhizobium tropici* allow high yield production of a modified EPS in a bioreactor containing a monoculture of *Rhizobium tropici*. Use of multiple bioreactors in a modular system that is able to be both scaled to a specific user and easily transported will enable production and employment of the amendment on or near location of its employment. The modified EPS may be processed to produce a transportable dry concentrate that may be reconstituted prior to use. One advantage of ex situ production is elimination of competitive biological systems present in situ.

In a specific test, *Rhizobium tropici* ATCC® 49672 procured from the American Type Culture Collection, Manassas, Va., was rehydrated into a specified growth medium (#111 broth) with a pH of 7.2. The optimal growth conditions for biopolymer production were based on the incubation medium recommended by the ATCC in 2007. The medium contains yeast extract, a soil extract, and mannitol ($C_6H_{14}O_6$) as a carbon source. The initial soil extract was prepared from African violet potting soil according to instructions supplied by ATCC®. The completed solution was autoclaved before use. Cultures were incubated aerobically at 30° C. The composition of the growth medium (#111 broth) is shown in Table 1.

TABLE 1

Composition of the AVS #111 broth.

| Ingredient | Amount | Composition | |
|---|---|---|---|
| Yeast Extract | 20 g | | |
| Mannitol | 200 g | | |
| Sodium carbonate | 4 g | | |
| DDI water | 16 L | | |
| Soil extract | 4 L | Total nitrogen (N) - 0.12%: | Ammoniacal N - 0.05% |
| | | | Nitrate N - 0.03% |
| | | | Urea N - 0.04% |
| | | Phosphate - 0.09% | |
| | | Soluble potash - 0.07% | |

Figure 3:
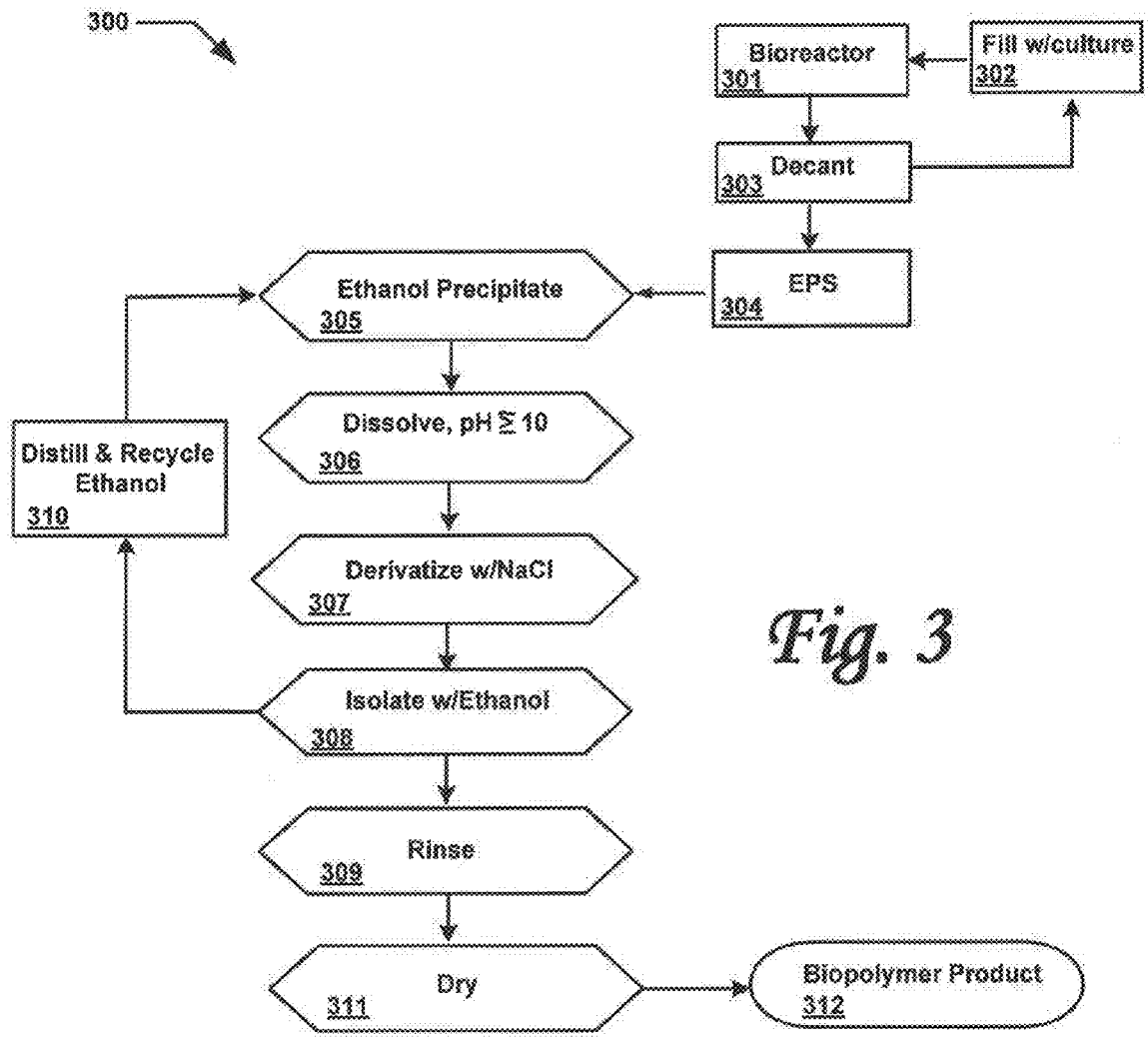
FIG. 3 is a flow diagram of a process for making select embodiments of the present invention.

Refer to FIG. 3 depicting a flow chart 300 of the process for producing select embodiments of the present invention ex situ. The bioreactor 301 is filled 302 with culture. A portion is decanted 303 and provided as the EPS 304 and the remainder is re-cycled to the bioreactor 301 together with any makeup culture needed to fill 302 the bioreactor 301. The EPS 304, after decanting 303 from the cultures, is precipitated 305 from solution by mixing it at a volume ratio of 1:2 ethanol to the mixture of EPS and water. Solid EPS is allowed to precipitate from the EPS-ethanol:water solution 305 overnight and the excess ethanol:water solution removed. The resulting biopolymer precipitate is re-hydrated 306 at a pH of greater than about 10 and preferably 12, with distilled, deionized water (DDW) and 0.05 grams of sodium chloride (NaCl) added 307 to the re-hydrated solution to form a biopolymer salt. This volume of material is added 308 to two volumes of ethanol allowing the salt of the hydrolyzed biopolymer to settle. The ethanol:water solution is distilled and recycled 310 and the recovered biopolymer salt rinsed 309 with multiple washings of ethanol and allowed to dry 311 overnight. This process yields a dry salt of the original biopolymer as product 312. This process is amenable to scale up for production of large quantities of product 312.

Characterization of the EPS was done first by size exclusion chromatography. Samples were loaded onto a 1.5×30-cm size exclusion column and eluted at 0.5-mL/min in 10-mM ammonium acetate at a pH of 5.5. Detection was accomplished by means of a Knauer refractive index detector. Retention times were compared to dextran standards of 10-kD, 167-kD, and 511-kD molecular weight. Next, the EPS was characterized by glycosyl composition analysis performed by combined gas chromatography/mass spectrometry (GC/MS) of the per-O-trimethylsilyl (TMS) derivatives of the monosaccharide methyl glycosides produced from the sample by acidic methanolysis using procedures described in Merkle and Poppe. Merkle, R. K. and I. Poppe, Carbohydrate Composition Analysis of Glycoconjugates by Gas-Liquid Chromatography/Mass Spectrometry, Methods Enzymol. 230, 1-15, 1994. GC/MS analysis of the TMS methyl glycosides was performed on an HP 5890 GC interfaced to a 5970 MSD, using an Alltech EC-1 fused silica capillary column (30-m×0.25-mm ID). The EPS was also characterized by glycosyl linkage analysis in which the sample was permethylated, depolymerized, reduced, and acetylated. The resulting partially methylated alditol acetates (PMAAs) were analyzed by GC/MS as described by York et al. York, W. S., et al., Isolation and Characterization of Plant Cell Walls and Cell Wall Components, Methods Enzymol., 118, 3-40, 1985. The EPS was also characterized by NMR spectroscopy. The sample was deuterium-exchanged by lyophilization from $D_2O$ (99.9% D), dissolved in 0.7-mL $D_2O$ (99.96% D), and transferred to a 5 mm NMR tube (Wilmad). 1-D Proton and 2-D TOCSY, NOESY, gradient enhanced COSY (gCOSY), gradient enhanced HSQC (gHSQC), and gradient enhanced HSQC-TOCSY (gHSQC-TOCSY) NMR spectra were acquired on a Vaarian Inova-500 MHz spectrometer at 343 K (70° C.). Chemical shifts were measured relative to internal acetone ($\delta_H$=2.225 ppm, $\delta_C$=31.07 ppm). Finally, surface tension was determined as a characteristic of the EPS. The height of a column of aqueous solution drawn into a capillary tube is proportional to the surface tension of the solution. The surface tension of the *Rhizobium tropici* EPS salt solution was compared to that of DDI water and another bacterium. See FIG. 2.

Potential use as a soil amendment required testing for hydraulic conductivity. EPS salt was added to clean sand at 0.33% by dry weight. Hydraulic conductivity was determined using the constant head permeability test with test parameters as given in Table 2. The constant-head method allows water to move through the soil under a steady-state head condition while the quantity of water flowing through the soil is measured over a period of time. Hydraulic conductivity was compared using three column lengths, 55 cm, 60 cm, and 65 cm.

TABLE 2

Test parameters.

| Test Parameters | Value |
|---|---|
| K (cm/sec) = Q * L/a * h * T | |
| Length of Specimen, L (cm) | 2.500 |
| Diameter of Specimen, D (cm) | 1.200 |
| Area of Specimen, a (cm$^2$) | 2.826 |
| Head height, h(cm) | 50 cm |
|  | 60 cm |
|  | 65 cm |
| Dry weight of specimen, W2−W1 (g) | 5.000 |
| Specific gravity (Gs) | 2.660 |

Chemical characterization of *Rhizobium tropici* EPS. Based on the dextran standards, the *Rhizobium tropici* EPS demonstrated a molecular weight over 511,000 D. The results of the glycosyl composition analysis are given in Table 3. The monosaccharides are identified by their retention times in comparison to standards and the carbohydrate character of these are authenticated by their mass spectra. The EPS is composed mostly of glucose with some galactose. Linkage analysis of this sample, like the composition analysis, suggests that the *Rhizobium tropici* EPS is quite complex. Most of the linkages observed are consistent with those of the EPS produced by *Sinorhizobium meliloti*. Skorupska, A. et al., Rhizobial Exopolysaccharides Genetic Control and Symbiotic Functions, Microbial Cell Factories 5, 7, 19 pp, 2006. However, major peaks are unaccounted for in this structure, such as the terminal galactopyranose, 3,4-linked glucopyranose and the 3,4,6-linked glucopyranose. The 3,4,6-linked glucopyranose was observed by NMR to be the site of attachment of both pyruvate and a glucose residue not seen in *S. meliloti*. By NMR, the structure of this extracellular polysaccharide also appears to be similar to the succinoglycan from *R. meliloti* described by Chouly, C. et al (1995). Chouly, C. et al., NMR Studies of Succinoglycan Repeating-Unit Octasaccharides from *Rhizobium meliloti* and *Agrobacterium radiobacter*, Int. J. Biol. Macromol. 17, 357-363, 1995. However, a few differences were observed in the NMR analysis from the published structure.

The EPS produced by *Rhizobium tropici* grown in a lab displayed the same basic repeating structure of other Rhizobial EPS. Research has established that EPS from different strains of the same species often have variations in EPS structure although the basic repeating unit is the same. Canter Cremers et al., Unusual Structure of the Exopolysaccharide of *Rhizobium leguminosarum* bv. *viciae* Strain 248, Carbohydr. Res. 218, 185-200, 1991; Amemura and Hardata (1983); Dudman et al., (1983a, 1983b); Franzen et al. (1983).

TABLE 3

*Rhizobium tropici* EPS glycosyl linkage analysis

| Glycosyl Residue | Area | Percentage Present |
|---|---|---|
| Terminal galactopyranose | 17630582 | 1.7 |
| 3 linked glucopyranose | 117060862 | 11.6 |
| 3 linked galactopyranose | 57791861 | 5.7 |
| 6 linked glucopyranose | 36719123 | 3.6 |
| 4 linked glucopyranose | 118023243 | 11.7 |
| 3,4 linked galactopyranose | 27275239 | 2.7 |
| 2,3 linked galactopyranose | 22033572 | 2.2 |
| 3,4 linked glucopyranose | 75103353 | 7.4 |
| 2,4 linked galactopyranose | 32306217 | 3.2 |
| 3,6 linked glucopyranose | 91017884 | 9.0 |
| 4,6 linked glucopyranose | 174923085 | 17.3 |
| 4,6 linked galactopyranose | 24430079 | 2.4 |
| 3,4,6 linked glucopyranose | 105586225 | 10.5 |
| 2,4,6 linked glucopyranose | 51368581 | 5.1 |
| 2,3,6 linked galactopyranose | 18238690 | 1.8 |
| 2,3,6 linked glucopyranose | 15682677 | 1.6 |
| 2,3,4,6 linked glucopyranose | 23074469 | 2.3 |
| Sum | | 100 |

The production of the biopolymer in bioreactors with monoculture is attractive because of the high yield of polymer that can be obtained in the absence of competitive and predatory actions of other bacterial species in situ. Initial efforts to produce a biopolymer resulted in solid materials that did not have the hydroscopic, gel forming, and swelling nature noted for the EPS biopolymer prior to water removal. Polymer cross-linking as a result of condensation reactions between carboxylic acid and amine functionalities may produce much larger polymers with lower hydrophilicity upon water removal. McMurray, J., Organic Chemistry, Third Edition, Brooks/Cole Publishing Company, Pacific Grove, Calif., pp. 1049-1050, 1992.

In order to reduce or eliminate these reactions, derivatization of the majority of the carboxylic acid functional groups along the EPS biopolymer was achieved by elevating the solution pH and then adding NaCl. Under these conditions, it is surmised that deprotonation of the carboxylic acid groups and ion pairing, prior to precipitation using ethanol, results in a biopolymer salt. In such a form, the reaction between amines and carboxylic acid groups to produce cross linkages is thought to be reduced. When reconstituted in water, the dried salt produced in this manner quickly forms gels similar to those formed by the EPS biopolymer prior to drying. This technique provides a means of producing a low weight solid material that can easily be transported for onsite use employing local water sources for its reconstitution. Upon reintroduction to the soil, the sodium salt will be available for proton or other cation-exchange, fixating the biopolymer within the soil.

One useful property of the *Rhizobium tropici* EPS salt is its unique surface tension. Refer to FIG. 2. Compared to distilled water 203, the *Rhizobium tropici* biopolymer salt solution 201, measured using height solution in borosilicate class capillaries, indicated reduced surface tension. The reduced surface tension translates into enhanced wetting of soils and greater viscosity for biopolymer solutions relative to water. A 0.33% by mass solution of *Rhizobium tropici* 201 has a viscosity that is significantly greater than that of water 203. A 1% solution of the *Rhizobium tropici* EPS salt took the form of a non-fluid gel. The upper end solubility of the *Rhizobium tropici* biopolymer salt in water appears to be bounded by the formation of a gel.

Figure 4:
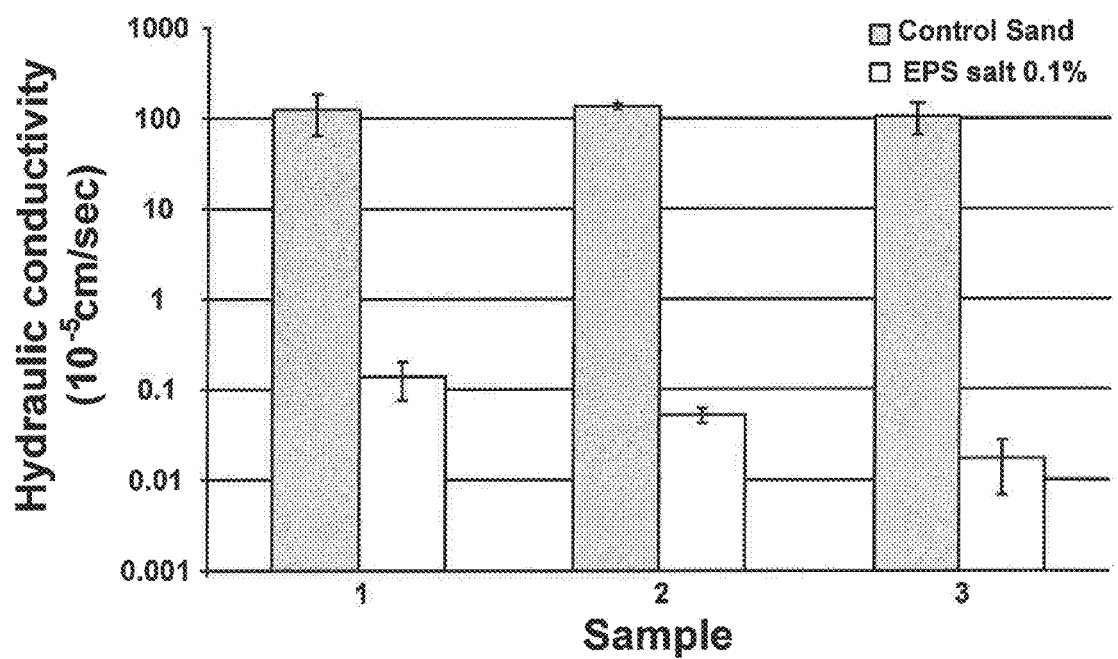
FIG. 4 presents test results for hydraulic conductivity of sand supplemented with a select embodiment of the present invention versus a control sand.
Figure 5:
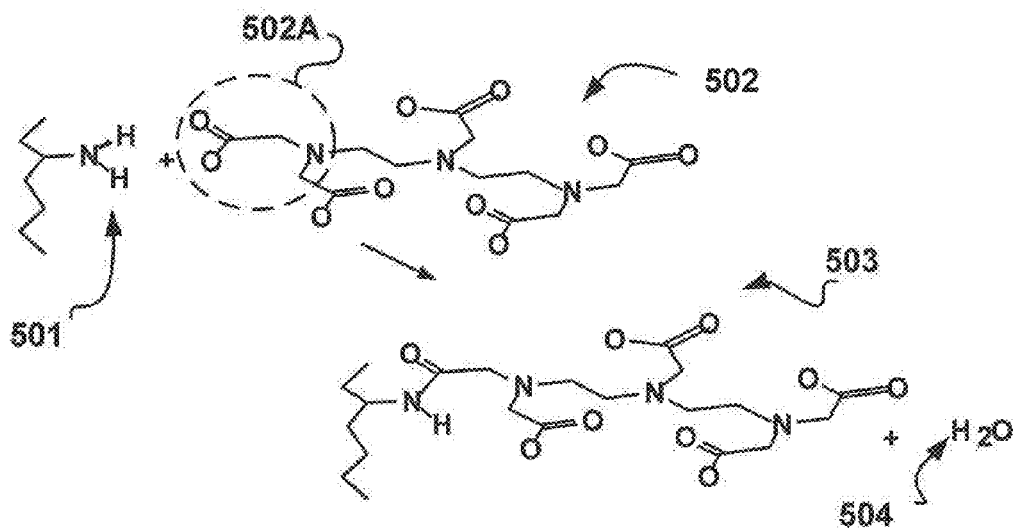
FIG. 5 depicts the natural reaction of *Rhizobium tropici* that produces a biopolymer.

Select embodiments of the present invention were tested for use as a soil amendment. The results of the hydraulic conductivity testing are shown in FIG. 4 and detailed in Table 4. Hydraulic conductivity for water in the control sand was $1.22 \times 10^{-3}$ compared to $7.57 \times 10^{-7}$ for water in the sand amended with the EPS salt, greater than three orders of magnitude reduction.

TABLE 4

Calculation of hydraulic conductivity by the constant-head method

| Condition | Sample | Q (cm$^3$) | t (sec) | Q * L | A * h * t × 10$^5$ | k × 10$^{-5}$ (cm/s) | Average × 10$^{-5}$ | SD × 10$^{-5}$ |
|---|---|---|---|---|---|---|---|---|
| Sand | 1 | 83.27 | 600 | 208.18 | 1.10 | 189 | 162 | 23.4 |
| h = 65 cm | 2 | 64.85 | 600 | 162.13 | 1.10 | 147 | | |
| | 3 | 66.10 | 600 | 165.25 | 1.10 | 150 | | |
| 0.1% BP in sand, | 1 | 11.08 | 86400 | 27.70 | 159 | 0.175 | 0.188 | 0.0135 |
| h = 65 cm | 2 | 12.83 | 86400 | 32.08 | 159 | 0.202 | | |
| | 3 | 11.96 | 86400 | 29.89 | 159 | 0.188 | | |
| Sand, | 1 | 48.04 | 600 | 120.10 | 1.02 | 1183 | 114 | 15 |
| h = 60 cm | 2 | 51.35 | 600 | 128.38 | 1.02 | 126 | | |
| | 3 | 39.48 | 600 | 98.70 | 1.02 | 97.0 | | |
| 0.1% BP in sand, | 1 | 3.97 | 88800 | 9.93 | 151 | 0.0659 | 0.0413 | 0.0286 |
| h = 60 cm | 2 | 5.67 | 173400 | 14.18 | 294 | 0.0482 | | |
| | 3 | 0.54 | 80400 | 1.35 | 136 | 0.00988 | | |
| Sand, | 1 | 25.67 | 600 | 64.18 | 0.933 | 68.8 | 91.2 | 37.1 |
| h = 55 cm | 2 | 49.98 | 600 | 124.95 | 0.933 | 134 | | |
| | 3 | 26.41 | 600 | 66.03 | 0.933 | 70.8 | | |
| 0.1% BP in sand, | 1 | 9.28 | 85200 | 23.20 | 132 | 0.175 | 0.0874 | 0.0782 |
| h = 55 cm | 2 | 3.31 | 84900 | 8.28 | 132 | 0.0627 | | |
| | 3 | 0.22 | 14400 | 0.55 | 22.4 | 0.0246 | | | where:
Q, quantity of water to be measured
t, time required for that quantity of water to be discharged
h, head height
L, measured length of the soil to be traveled
A, cross-sectional area of the soil specimen
K, hydraulic conductivity
BP, biopolymer salt of *Rhizobium tropici*

Table 5 examines the relationship between hydraulic conductivity and the potential for erosion (erodibility). The experimentally-derived hydraulic conductivity values for the control sand and the EPS-amended sand place them in appropriate classes for sands and clays. Stone, R. P., Vegetated Filter Strip System Design Manual, Ontario Ministry of Agriculture, Food and Rural Affairs, 2008; United States Department of Agriculture, Natural Resources Conservation Service, Soil Survey Manual, Chapter 3, Examination and Description of Soils, 2008. This is supported by the work of Zeleke and Si who reported that, on the observation (small) scale, variability in soil hydraulic conductivity (K) is significantly related to both sand and silt content. Zeleke, T. B. and B. C. Si, Scaling Relationships Between Saturated Hydraulic Conductivity and Soil Physical Properties, SSSAJ 69, 1691-1702, 2005. On a larger scale, the hydraulic conductivity is related to clay and organic carbon content. However, these scales are interdependent. The hydraulic conductivity of the amended sand was actually lower than the range given for clays. Evaluating the hydraulic conductivity value and the soil class indicates that the soil erosion potential is higher for the amended sand. However, this does not take into account the high viscosity and adhesive characteristics of the EPS.

The erosion factors shown in Table 5 as the K factor (Kw and Kf) and the T factor are indicators of the potential for water erosion. The K Factor is used in the Universal Soil Loss Equation (USLE) and the Revised Universal Soil Loss Equation (RUSLE) to predict the average annual rate of soil loss by water erosion in tons per acre per year. The estimates are based primarily on percentage of silt, sand, and organic matter on soil structure and permeability. In general, the higher the value, the more susceptible the soil is to erosion by water. Kw indicates the erodibility of the whole soil and Kf indicates the erodibility of the fines fraction, i.e., material less than 2 mm. Note that polyacrylamide, a common soil amendment used for erosion control, also may reduce permeability in some soils but is highly effective as a rainfall erosion control agent. NRCS Code 450; Ajwa, H. A. and T. J. Trout, Polyacrylamide and Water Quality Effects on Infiltration in Sandy Loam Soils, Soil Sci. Soc. Am. J. 70, 643-650, 2006.

Wind erodibility groups are made up of soils that have similar properties affecting their susceptibility to wind erosion in cultivated areas. University of Delaware, College of Agriculture and Natural Resources, Spatial Analysis Lab, accessed January, 2008. Susceptibility to wind erosion ranges from the most susceptible, Group 1, to least susceptible, Group 8. Group 1 consists of coarse sands, sands, fine sands, and very fine sands. Group 5 consists of non-calcareous loams and silt loams that are less than 20% clay and sandy clay loams, and sandy clays. Group 8 consists of rocky or wet soils that are not subject to wind erosion. As seen with the other erosion factors, the K value of the amended soil was so low that it actually counted as a sub-surface soil, and the erosion index is not representative.

TABLE 5

Effect of amendment of soil on erosion

| Soil | HC class | Viscosity | Surface water runoff potential 1-5% slope | Soil texture class | Erosion factor Kw | Kf | T | Wind erodibility group | Wind erodibility index |
|---|---|---|---|---|---|---|---|---|---|
| Control sand | Moderate | Low | Moderate | Loamy sand | 0.05 | nd | 5 | 1 | 310 |

TABLE 5-continued

Effect of amendment of soil on erosion

| Soil | HC class | Viscosity | Surface water runoff potential 1-5% slope | Soil texture class | Erosion factor | | | Wind erodibility group | Wind erodibility index |
|---|---|---|---|---|---|---|---|---|---|
| | | | | | Kw | Kf | T | | |
| Biopolymer amended sand | Very low | Very high | Very high | Clay | 0.37 | 0.37 | 4 | 5 | 56 |

On-site use of select embodiments of the present invention to stabilize soils and chelate heavy metals achieves appreciable cost savings. The use of traditional additives, e.g., lime, portland cement, petroleum based polymers and the like, costs from $0.25 to $1.05 per pound of product used, The total cost can vary dramatically depending on the soil conditions, the loading of stabilizer required, and application methods used. The cost of traditional petroleum-based additives continues to increase with the cost of petroleum. Select embodiments of the present invention demonstrate a reduction in lifecycle cost over both traditional and conventional non-traditional treatments due to several factors. These include: the ready "producibility" of a biopolymer; an inexpensive "green" production process train that results in minimal waste; transportation of a lighter, stable, dry material; inherent water retention properties and the transportability of "portable" bioreactors to produce product on-site. Further, because synthetic polymers persist in the soil, treatment of berms, levees, embankments, impact areas and the like may require expensive treatment for reuse, whereas with biopolymers, reapplication of biopolymer or reuse of treated soil does not pose any environmental or performance issues.

Cost-effective dust and erosion control on bermed and unbermed SAFRs and OB/OD ranges may be obtained with select embodiments of the present invention. Range operators spend significant amounts of time re-surfacing berms as a result of rutting and washout of impact areas following a heavy rain. The conventional approach to erosion control on steep banks is vegetation and reinforcement. Vegetation is difficult to maintain as projectile impacts often prevent the sustainment of a vegetative stand near target areas. Reinforcement with incompressible materials such as riprap, conventional portland cement-based concrete or stone presents a ricochet hazard. Select embodiments of the present invention provide a soil stabilization approach to SAFR management as bullet impacts will ultimately damage any solid material. An additional application of select embodiments of the present invention plus water, as needed, or water alone, promotes stabilizing cross linkages, initiating a self-healing process. Select embodiments of the present invention are easily applied by range operators as a dry powder or gelled polymer water mixture.

In summary, the biopolymer produced by *Rhizobium tropici* may be cultivated in batch bioreactors and modified to yield a readily transportable salt that precipitates from solution and can be re-hydrated back to its original form. A 0.33% solution of the salt reduces surface tension more than three times relative to water. When an EPS salt represented by select embodiments of the present invention is added to soil at 0.1% by dry weight, this amendment significantly decreases the hydraulic conductivity of the soil. The values are similar to that produced by amending with synthetic polymers, but the *Rhizobium tropici* polymer is biodegradable and production does not produce non-biodegradable waste. These properties make the biopolymer an attractive, "green" alternative to synthetics for use in construction, in particular for addressing soil erosion and stability requirements.

We claim:

1. A dry salt comprising a biopolymer of at least an extracellular polymeric substance EPS naturally produced by *Rhizobium tropici*, said dry salt made by:
   placing a culture of said *Rhizobium tropici* in at least one container of water and nutrients;
   maintaining said culture and said water-nutrient mixture for a pre-specified hold time to produce a first mixture comprising at least said water and said EPS;
   decanting said first mixture to yield said EPS and an aqueous fluid;
   precipitating said EPS with an alcohol to yield a first precipitate;
   adding to each said first precipitate at least one hydroxide to dissolve said first precipitate by mixing said hydroxide with said first precipitate to yield a homogeneous second mixture with a pH above about 10;
   derivatizing said second mixture by adding at least one solid first salt, mixing said first salt with said second mixture to establish a homogeneous third mixture;
   isolating said third mixture in an alcohol to yield a second precipitate;
   decanting said alcohol, leaving at least said second precipitant;
   rinsing said second precipitant at least once; and
   drying said rinsed second precipitant to yield said dry salt.

2. The dry salt of claim 1 in which said container is at least one bioreactor.

3. The dry salt of claim 1 in which said *Rhizobium tropici* is a catalogued symbiotic nodulator of leguminous plants.

4. The dry salt of claim 1 in which said first solid salt is NaCl.

5. The dry salt of claim 1 in which said alcohol is ethanol added in the volume ratio of approximately 1:2 said ethanol to said third mixture.

6. The dry salt of claim 1 in which said hydroxide is added in a quantity to yield a pH above about 10.

7. The dry salt of claim 1 in which:
   said water is distilled deionized water;
   said nutrients comprise at least:
      yeast extract;
      sodium carbonate;
      soil extract; and
      mannitol ($C_6H_{14}O_6$); and
   said first salt is added to provide a 0.1 normal sodium chloride solution.

8. The dry salt of claim 1 in which said EPS comprises at least one extracellular polysaccharide.

9. The dry salt of claim 1 in which said pre-specified hold time is about one hour.

10. A method of manufacturing a dry salt comprising a biopolymer of at least an extracellular polymeric substance EPS naturally produced by *Rhizobium tropici*, comprising:
    placing a culture of said *Rhizobium tropici* in at least one container of water and nutrients;
    maintaining said culture and said water-nutrient mixture for a pre-specified hold time to produce a first mixture comprising at least water and said EPS;
    decanting said first mixture to yield said EPS;
    precipitating said EPS with an alcohol to yield a first precipitate;
    adding to each said first precipitate at least one hydroxide to dissolve said first precipitate by mixing said hydroxide with said first precipitate to yield a homogeneous second mixture with a pH above about 10;
    derivatizing said second mixture by adding at least one solid first salt, mixing said first salt with said second mixture to establish a homogeneous third mixture;
    isolating said third mixture in an alcohol to yield a second precipitate and an alcohol fluid;
    decanting said alcohol, leaving at least said second precipitant;
    rinsing said second precipitant at least once; and
    drying said rinsed second precipitant to yield said dry salt.

11. The method of claim 10 said *Rhizobium tropici* comprising a catalogued symbiotic nodulator of leguminous plants.

12. The method of claim 10 said container comprising at least one bioreactor.

13. The method of claim 10 said first solid salt comprising NaCl.

14. The method of claim 10 said alcohol comprising ethanol added in the volume ratio of approximately 1:2 said ethanol to said third mixture.

15. The method of claim 10 adding said hydroxide in a quantity to yield a pH above about 10.

16. The method of claim 10 providing:
    said water as distilled deionized water;
    said nutrients as at least:
        yeast extract;
        sodium carbonate;
        soil extract; and
        mannitol ($C_6H_{14}O_6$); and
    said first salt to yield a 0.1 normal sodium chloride solution.

17. The method of claim 10 further comprising re-cycling said aqueous fluid to said container for use in subsequent batch processing.

18. The method of claim 10 further comprising distilling and re-cycling said alcohol fluid for re-use in precipitating said EPS in subsequent batch processing.

19. The method of claim 10 providing said EPS as at least one extracellular polysaccharide.

20. The method of claim 10 said pre-specified hold time comprising about one hour.

21. A soil amendment, comprising:
    a dry salt comprising a biopolymer of at least an extracellular polymeric substance EPS naturally produced by *Rhizobium tropici*, said dry salt made by:
        placing a culture of said *Rhizobium tropici* in at least one container of water and nutrients;
        maintaining said culture and said water-nutrient mixture for a pre-specified hold time to produce a first mixture comprising at least water and said EPS;
        decanting said first mixture to yield said EPS and an aqueous fluid;
        precipitating said EPS with an alcohol to yield a first precipitate;
        adding to each said first precipitate at least one hydroxide to dissolve said first precipitate by mixing said hydroxide with said first precipitate to yield a homogeneous second mixture with a pH above about 10;
        derivatizing said second mixture by adding at least one solid first salt, mixing said first salt with said second mixture to establish a homogeneous third mixture;
        isolating said third mixture in an alcohol to yield a second precipitate;
        decanting said alcohol, leaving at least said second precipitant;
        rinsing said second precipitant at least once; and
        drying said rinsed second precipitant to yield said dry salt; and
    an aqueous solution to activate said dry salt.

22. A method for amending soil, comprising:
    providing a dry salt comprising a biopolymer of at least an extracellular polymeric substance EPS naturally produced by *Rhizobium tropici*, said dry salt made by:
        placing a culture of said *Rhizobium tropici* in at least one container of water and nutrients;
        maintaining said culture and said water-nutrient mixture for a pre-specified hold time to produce a first mixture comprising at least water and said EPS;
        decanting said first mixture to yield said EPS and an aqueous fluid;
        precipitating said EPS with an alcohol to yield a first precipitate;
        adding to each said first precipitate at least one hydroxide to dissolve said first precipitate by mixing said hydroxide with said first precipitate to yield a homogeneous second mixture with a pH above about 10;
        derivatizing said second mixture by adding at least one solid first salt, mixing said first salt with said second mixture to establish a homogeneous third mixture;
        isolating said third mixture in an alcohol to yield a second precipitate;
        decanting said alcohol, leaving at least said second precipitant;
        rinsing said second precipitant at least once; and
        drying said rinsed second precipitant to yield said dry salt; and
    mixing said dry salt with said soil to amend said soil.

23. The method of claim 22 further comprising adding an aqueous solution to activate said dry salt.

24. The method of claim 23 further comprising adding said aqueous solution to said dry salt prior to mixing said dry salt with said soil.

25. The method of claim 22 further comprising mixing said dry salt with said soil at a weight ratio of about 1:1000, said dry salt to said soil.

* * * * *